(12) United States Patent
Snoke et al.

(10) Patent No.: US 11,977,010 B2
(45) Date of Patent: May 7, 2024

(54) METHOD AND APPARATUS FOR DISLODGING CORE TISSUE BIOPSY SAMPLES FROM CORE COLLECTORS AND FOR STORING AND PREPARING SAMPLES FOR PATHOLOGY

(71) Applicant: URO-1, Inc., Greensboro, NC (US)

(72) Inventors: Phillip Jack Snoke, Winston-Salem, NC (US); Sharon Collins Presnell, Winston-Salem, NC (US); Philip Morrison Allred, III, Kernersville, NC (US); Ted Belleza, LaSelva Beach, CA (US)

(73) Assignee: URO-1, Inc., Greensboro, NC (US)

( * ) Notice: Subject to any disclaimer, the term of this patent is extended or adjusted under 35 U.S.C. 154(b) by 299 days.

(21) Appl. No.: 17/518,442

(22) Filed: Nov. 3, 2021

(65) Prior Publication Data
US 2023/0134295 A1    May 4, 2023

(51) Int. Cl.
G01N 1/00   (2006.01)
A61B 10/00  (2006.01)
G01N 1/36   (2006.01)

(52) U.S. Cl.
CPC ........... *G01N 1/36* (2013.01); *A61B 10/0096* (2013.01)

(58) Field of Classification Search
None
See application file for complete search history.

(56) References Cited

U.S. PATENT DOCUMENTS 5,080,869 A * 1/1992 McCormick ........... G01N 1/312
                                              422/547
6,017,476 A * 1/2000 Renshaw ................ G01N 1/36
                                              425/117
7,156,814 B1 * 1/2007 Williamson, IV ..........................
                                              A61B 10/0096
                                              435/297.5
7,914,738 B2 * 3/2011 Hutchins ................. G01N 1/36
                                              422/65
8,329,120 B2 * 12/2012 Williamson, IV ..........................
                                              G01N 33/4833
                                              206/486
8,383,067 B2 * 2/2013 Williamson, IV ....... G01N 1/31
                                              435/40.5
9,341,551 B2    5/2016 Pasternak et al.
10,383,607 B2   8/2019 Pasternak et al.
10,794,804 B2 * 10/2020 Williamson, IV ....... G01N 1/36
(Continued)

FOREIGN PATENT DOCUMENTS

CN    208981996    6/2019
WO    2023081272   5/2023

OTHER PUBLICATIONS

European Extended Search Report for EP 22 20 5258, completed Mar. 6, 2023.
(Continued)

*Primary Examiner* — Brandi N Hopkins
*Assistant Examiner* — Nigel H Plumb
(74) *Attorney, Agent, or Firm* — Wissing Miller LLP (57) ABSTRACT

A tissue core sample in a metal core collector or stylet is touched to a substrate channel filled with as special liquid such as a hydrogel to which the tissue core sample is attracted to thereby transfer the tissue sample to the channel while preserving the integrity of the sample, speeding up the transfer and preserving the sample orientation so it can be unambiguously associated with its anatomical origin.

30 Claims, 7 Drawing Sheets

(56) References Cited

U.S. PATENT DOCUMENTS

| | | |
|---|---|---|
| 2005/0112037 A1 | 5/2005 | Darling |
| 2007/0116612 A1 | 5/2007 | Williamson, IV |
| 2017/0100103 A1* | 4/2017 | Stone ................. A61B 10/0096 |
| 2018/0120308 A1* | 5/2018 | Musat ................. G01N 33/5436 |
| 2022/0134330 A1* | 5/2022 | Titcombe ............. B01L 3/5055 |
| | | 422/536 |

OTHER PUBLICATIONS

International Search Report and Written Opinion for PCT/US2022/048807, dated Feb. 28, 2023.

* cited by examiner

METHOD AND APPARATUS FOR DISLODGING CORE TISSUE BIOPSY SAMPLES FROM CORE COLLECTORS AND FOR STORING AND PREPARING SAMPLES FOR PATHOLOGY

FIELD

This patent specification relates to dislodging core tissue biopsy samples from a core collector and to cassettes for core tissue samples and methods of loading tissue samples therein, preparing the samples for delivery to a pathology laboratory, and to kits for handling and shipping core tissue biopsy samples.

BACKGROUND

Figure 12A:
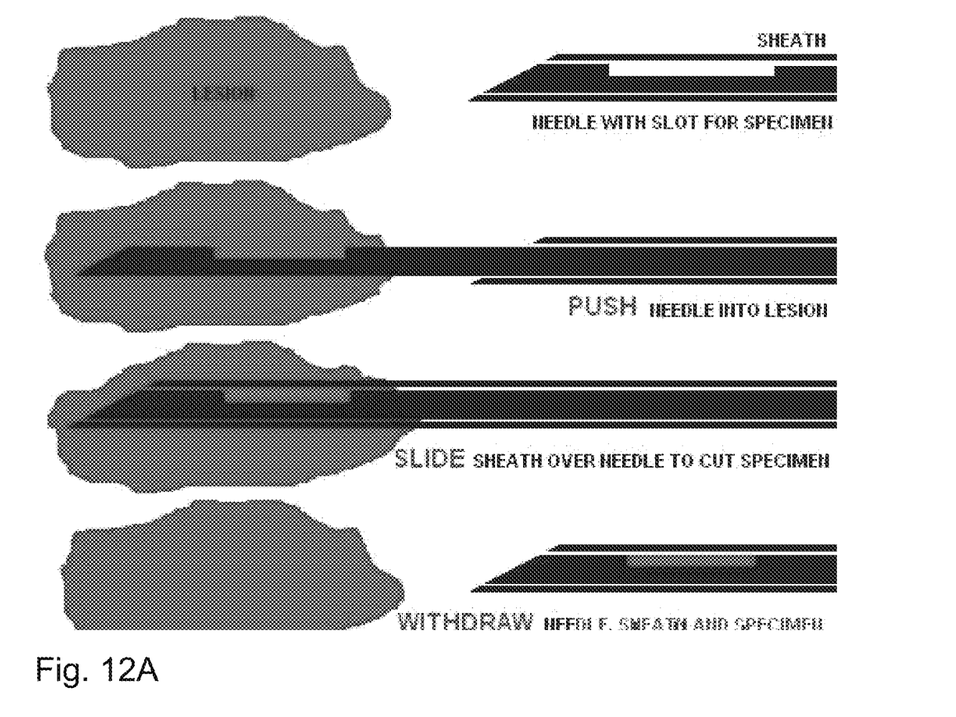
FIG. 12A illustrates a known method of taking a tissue sample with a core collector needle.
Figure 12B:
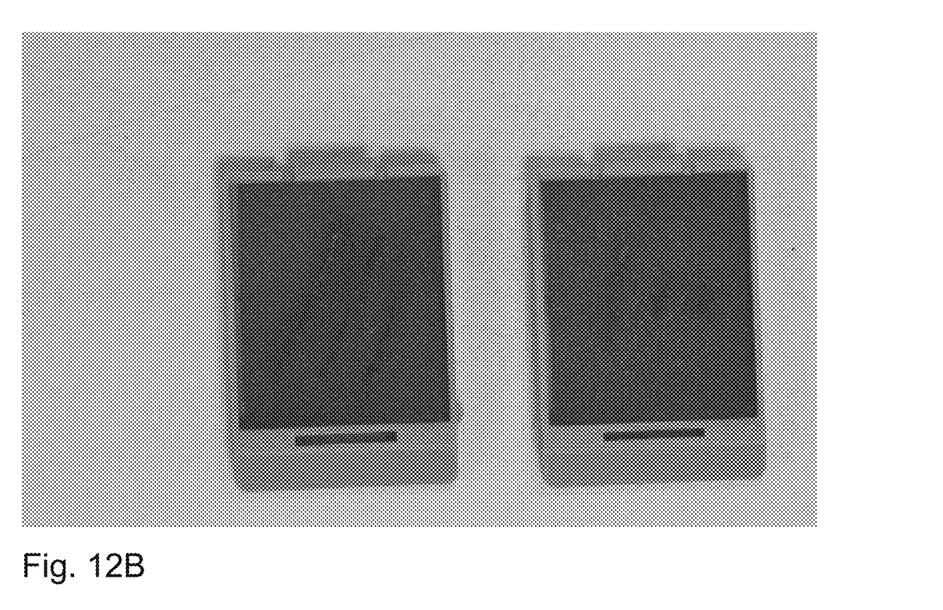
FIG. 12B illustrates tissue samples deposited on known foam pads.

Core biopsy is a well-known medical procedure. FIG. 12A shows one example of steps in collecting a tissue sample with a core biopsy instrument. The instrument initially houses a core collector A1 of a core biopsy needle, sometimes called only a core collector or a coring needle or stylet, in a sheath A2. Core collector A1 is spring loaded and fired out of sheath A2 and into tissue A3. A sample of tissue protrudes into a slot or cutout A4 near the distal end of core collector A1, and then the instrument fires sheath A2 over core collector A1. The sharp distal end of sheath A2 cuts the tissue A5 that has protruded in slot A4 from surrounding tissue to thereby separate a core tissue sample A5. The physician withdraws core collector A1 together with sheath A2 from the patient and hands the instrument to an assistant. The assistant pulls back sheath A2 to expose the core tissue sample A5 and wipes, sometimes repeatedly, the open side of slot A4 on a foam pad, GAUZE, Tefla pad or similar material to thereby deposit the tissue sample A5 thereon. The assistant then cocks the spring-loaded instrument to prepare it for taking another sample and hands it back to the physician if additional samples need to be taken. FIG. 12B illustrates two known foam pads B1 in cassettes B2, with several tissue samples on the pads (only one of the samples is labeled A5). The assistant covers the tissue sample on foam pad B1 with another foam pad (not shown) or a membrane permeable to tissue fixative and places the sealed cassette B2 in a bottle of tissue fixative for delivery to pathology. In the example of prostate core biopsy, a typical transrectal systematic biopsy involves samples from the parasagittal plane on the right and left sides of the base, midzone, and apex, with each site arbitrarily assigned by the operator. Known current procedures typically involve extracting 12 to 16 or more cores per biopsy, often from the standard sextant and other areas of the peripheral, transition, or anterior zones. The optimal number and location of core samples are not standardized and vary based on individual preferences and experience. In the example of breast biopsy, typically tissue samples are taken from lesion locations that have been previously found through imaging modalities such as x-ray, ultrasound, and MRI. Core biopsies also are used for other organs and tissue such as liver, kidneys and breasts.

In known current practice, the assistant typically wipes the distal portion of the core collector on the foam pad to dislodge the sample from the core collector and might use tweezers to help remove the sample from the core collector or to reposition the sample on the foam pad. The tissue sample fits snugly in the core collector and can be slightly compressed therein, making it difficult in some cases to remove and requiring manipulations that may deform it. The tissue sample may not simply fall out of the core collector by shaking and thus removal in the standard process involves swiping on a foam pad or filter paper or the like and possibly using forceps or another tool to remove the sample from the core collector and straighten it on the foam pad or the like. FIG. B illustrates two foam pad cassettes with core tissue samples. In this figure, three core samples are in each cassette although in typical practice each cassette would hold only a single core sample. Dislodging a tissue sample from a core collector needle onto a foam pad may not preserve sample integrity and may result in artifacts such as compression, tearing, and twisting that may interfere with subsequent examination. Dipping and swishing to dislodge a tissue sample from a core collector also have been used or proposed.

The submission of a high-quality core sample to a pathologist is a crucial component for a successful pathologic evaluation. It is important to preserve core sample integrity and orientation to ensure that the diagnostic sample delivered to a pathologist accurately represents the patient's tissue in situ with respect to the position, size, shape, and orientation of a lesion and the cells therein. It is desirable for the core tissue sample to remain intact, as close as practicable to the way it was while in its anatomical origin. However, the known process described above for depositing core samples on foam pads is a delicate operation that is difficult to perform with good or consistent results and may not preserve core sample integrity. The current gold-standard process of depositing a core tissue sample on a foam pad or the like tends to introduce artifacts in the sample due to stretching, folding, tearing, or compression of the tissue during sample processing. For example, the tissue samples in FIG. B show tortuosity and poor integrity, which can make pathology interpretation difficult and less reliable. Core volume and integrity are important particularly where tissue architecture in the sample is paramount, such as in samples of non-malignant liver (e.g., cirrhosis) and non-malignant kidney (e.g., glomerulonephritis). Proposals for a cassette that accepts a plurality of tissue samples are discussed in U.S. Pat. Nos. 5,002,377, 5,127,537 and 10,670,593 and in published applications US 201/067338 A1 and US 2019/0060893A1. To applicant's knowledge, they have not been translated into commercial products and put into practical use. U.S. Pat. No. 10,670,593 discusses a protein matrix for receiving multiple tissue samples and one example is a matrix hydrated to make it flexible and driven over a roller such that channel openings widen and an adhesive at the channel bottoms would hold sample in place despite the widened openings.

SUMMARY OF DISCLOSURE

This patent specification describes a new system and method for retrieving biopsy tissue samples or specimens from a biopsy core collector, submerging them in a fixative solution, and storing them for transport to a pathology lab for analysis in a manner which preserves tissue integrity and improves the diagnostic value of core tissue samples such as from core biopsies of the prostate. In the new system and method, a cassette is made of a material such as polymer or an injection molded plastic and has one or more liquid-lined channels, each sized and shaped to accept a core tissue sample from a core collector. This new approach can standardize and reduce variability of retrieval methods as well as accelerate sample processing at the point of collection (clinic) and in the pathology laboratory.

Notably, a special liquid in the channel has the requisite chemical and physical properties to sufficiently attract and retrieve the tissue sample on contact, enabling facile removal from the sample collection device (core collector) while preserving tissue integrity and orientation. The term special liquid is used in this patent specification to refer to a substance that is hydrophilic and can be a liquid, colloidal, or hydrogel solution, suspension, or dispersion that has the properties of being hydrous and hydrophilic and further has the special properties that are described below and result in the ability to attract a tissue sample from a core collector in a touch-and-go motion and to easily release the tissue sample when needed. The physician or assistant gently contacts the exposed axis of a core tissue sample that is contained within a core collector (needle) to the liquid-lined channel. The special liquid is designed to exert cohesive forces on the exposed surface of the tissue sample in the core collector, resulting in the tissue dislodging from the core collector and attaching preferentially to the special liquid in the liquid-lined channel. Moreover, the attraction of the tissue to the liquid-lined inside wall of the channel ensures retention of the special liquid in the channel and thus retention of the tissue sample in the channel. Importantly, the attachment of the tissue sample to the channel is a non-covalent and non-permanent, driven primarily by gentle and transient surface tension and hydrostatic forces, such that the tissue sample can detach easily from the liquid-lined channel as required for secondary tissue processing. Simply lining up the core collector to the channel and lightly touching the tissue sample to the liquid in the channel transfers an intact and undamaged core sample to the channel, and the sample can be easily taken out of the channel for further processing and assessment in a pathology lab. An important advantage of this new approach is the ability to easily capture the tissue from the core collector at the collection point (clinic) and subsequently release it easily at the processing point (pathology lab) without requiring further processes to uncouple the tissue sample from the channel using mechanical, enzymatic, or other special means. The coherence of the special fluid lining the channel to the channel wall is greater than the coherence of this special fluid to the tissue sample and is greater than the coherence of the tissue sample to the inside wall of the core collector. The new approach leverages differences in sources of cohesion and adherence among the tissue sample, the inner wall of the core collector, a special liquid, and the inner wall of a channel in a cassette. Preferably, the material forming the inner wall of the channel is sufficiently hydrophilic to allow the special liquid to line it.

As noted, the term special liquid as used in this patent specification differentiates from solid material and refers to substances that at room temperature are more viscous than water and encompasses suspensions or solutions of solid materials such as gels and hydrogels and liquids that are so viscous that they stay in a channel when smeared thereon. The special liquids referred to this this patent specification have the important properties described above that result in attracting a tissue sample from a core collector and holding the sample in the channel but easily releasing the tissue sample from the channel when needed rather than acting as an adhesive that makes release from the channel so difficult that the sample would be damaged or distorted by the release.

Significant advantages of the new approach described in this patent specification include: (1) improved tissue sample integrity (compared to known current standard devices/methods), with fewer collection-related and processing-related tissue sample artifacts that interfere with diagnostic use such as tearing, folding, and compression; (2) acceleration of sample processing, both primary (point of collection—tissue to channel in cassette) and secondary (pathology lab) tissue sample processing (cassette to slide); and (3) improved diagnostic value, with preservation of tissue integrity and orientation so that samples can be easily and unambiguously associated with their anatomical origin, with improved usability (e.g., in the current known gold standard methods typically a certain percentage of the samples are unusable due to loss or to collection-related artifacts but the new approach yields a much higher percentage of usable samples, thereby offering substantial improvement in the pathological diagnostic value to the patient and physician).

According to some embodiments, a system comprises: a tissue core sample cassette having a base with a channel configured to hold a tissue sample and filled with a special liquid that comprises a hydrogel; said cassette further comprises a removable membrane covering the channel that keeps the liquid therein and a lid hinged to the base and configured to pivot between open and closed positions; wherein: said lid has an array of through holes that are over said channel when the lid is closed and further has a bottom surface that surrounds the array of holes and when the lid is closed is flush with an upper surface of the base that surrounds the channel therein; said lid is configured to snap-fit to the base when closed over said membrane and to open and expose the membrane when manually pushed from the base; said liquid is exposed when the lid is moved from being closed over the membrane to being open and the membrane is peeled off; and said liquid has the property of attracting a tissue sample touched thereto and keeping a tissue sample in the channel, being soluble in tissue fixative, and free of substances adversely affecting sample characteristics; said lid is transparent and has a pattern of visible markings along said array of through holes that are spaced by selected distance, to facilitate grossing a tissue sample in the channel while the lid is closed; and said lid when closed over a tissue sample in the channel is configured for flow of tissue fixative through said holes to the sample. Gross processing or "grossing" is the process by which pathology specimens undergo examination with the bare eye to obtain diagnostic information, prior to cutting and tissue sampling to prepare material for subsequent microscopic examination.

According to some embodiments, the system can further include one or more of the following: (a) a plurality of said tissue sample cassettes forming a set of cassettes and a vessel having an internal cross-section matching an outside shape of said cassettes and configured to hold said set of cassettes stacked on each other and sealed while immersed in tissue fixative: (b) each of one or more of said cassettes is permanently pre-labeled with an identification of an anatomical and regional origin of a tissue sample according to a medical labeling convention; (c) the base of each of one or more of the cassettes in the set includes a hinge pin and the lid includes a rounded channel with that tightly fits over the hinge pin and has an opening configured to snap over the pin, wherein the lid and base are separately molded of respective polymeric materials and the lid is snapped over said pin to pivot about the pin between being open and closed; (d) the lid of each of one or more of the cassettes in the set includes an upward peripheral lip configured to pool formalin; (e) the lid of each of at least some of the cassettes in the set includes a downward peripheral lip configured to tightly fit over a periphery of the base; (f) the base of each of one or more some of the cassettes in the set includes a central opening that the lid clears, which central opening facilitates flow of tissue fixative such as formalin or other liquids bathing tissue samples in said cassettes when in said vessel; (g) the base of each of one or more of the cassettes in the set is generally round and is scalloped with two diametrically opposed finger-hold indentation to facilitate handling the cassette; (h) said upper surface of the base surrounding the channel is flat and said base has a generally hollow underside in each of one or more of the cassettes in the set; (i) the lid of each of one or more of the cassettes in the set has a flat underside surface surrounding said array of through holes; and (j) the lid may not be hinged to the base.

According to some embodiments, a tissue core sample cassette comprises: a base with an open channel configured to hold a tissue sample and configured to hold a special liquid that comprises a hydrogel; a lid hinged to the base and configured to pivot between being open and being closed; wherein: said lid has an array of through holes that are over said channel when the lid is closed and further has a bottom surface that surrounds the array of holes and when the lid is closed is flush with an upper surface of the base that surrounds the channel therein; said lid is configured to snap-fit to the base when closed and cover said channel with at least some of the holes over the channel and to open and expose the channel when manually pushed from the base; said lid is transparent and has a pattern of visible markings along said array of holes that are spaced by selected distance, to facilitate grossing of a tissue sample in the channel while the lid is closed; and said lid when closed over a tissue sample in the channel is configured for flow of tissue fixative through said holes to the sample.

According to some embodiments, the cassette described in the immediately preceding paragraph further includes one or more of the following: (a) the cassette includes special liquid filling the channel and a removable membrane covering the channel and keeping the liquid therein until being removed to expose the channel and the liquid; (b) said liquid has the property of attracting a tissue sample touched thereto and keeping a tissue sample in the channel, being soluble in tissue fixative, and free of substances adversely affecting sample characteristics; (c) said base includes a central opening configured for flow of tissue fixative therethrough; (d) said base is molded as a single piece and includes a hinge pin and said lid is separately molded as a single piece and includes a tubular catch with an opening configured to snap-fit over said hinge pin for pivoting thereabout; (e) said base is made of a polymeric material colored to contrast with a tissue sample in said channel; (f) said base is permanently pre-labeled with an identification of an anatomical origin of a tissue sample according to a medical labeling convention; and (g) said base includes one or more finger-hold indentations to facilitate handling the cassette at least when depositing a tissue sample in said channel.

According to some embodiments, a method of preparing tissue samples for sending to pathology comprises: touching exposed portions of respective tissue samples in core collector needles to a special liquid comprising hydrogel filling a channel in respective bases of cassettes to thereby dislodge the samples from the core collector needles into the respective channels; snapping and releasably locking a transparent lid over the channel and the sample therein in the respective cassettes; and stacking the cassettes with the samples therein and the lids closed in a vessel of tissue fixative having an interior shape conforming to and closely fitting the exterior shape of the stacked cassettes but providing sufficient space around the stacked cassettes for flow of tissue fixative up and down the vessel; and further providing central holes in said cassette bases for flow of tissue fixative in the vessel through said central holes in the bases of the cassettes stacked in the vessel.

According to some embodiments, the method can further include separately molding or otherwise forming the cassette bases as single pieces of polymeric materials in a color contrasting the tissue samples and the lids as single pieces of a hard transparent plastic. According to some embodiments, the method can include molding the cassette as a single piece of polymeric material, with the base and lid connected to each other with a living hinge formed as a part of the molding process such that the cassette can be easily closed after a tissue sample has been placed in the channel and opened later for visual grossing with appropriate markings to facilitate the process or for other purposes. This embodiment using a live hinge can make the process or manufacturing the cassette significantly less expensive than the process of molding or otherwise forming the base and lids as separate pieces and connecting them by snapping the lid into the hinge pins.

BRIEF DESCRIPTION OF THE DRAWINGS

To further clarify the above and other advantages and features of the subject matter of this patent specification, specific examples of embodiments thereof are illustrated in the appended drawings. It should be appreciated that these drawings depict only illustrative embodiments and are therefore not to be considered limiting of the scope of this patent specification or the appended claims. The subject matter hereof will be described and explained with additional specificity and detail through use of the accompanying drawings in which:

DETAILED DESCRIPTION

A detailed description of examples of preferred embodiments is provided below. While several embodiments are described, the new subject matter described in this patent specification is not limited to any one embodiment or combination of embodiments described herein, but instead encompasses numerous alternatives, modifications, and equivalents. In addition, while numerous specific details are set forth in the following description to provide a thorough understanding, some embodiments can be practiced without some or all these details. Moreover, for the purpose of clarity, certain technical material that is known in the related art has not been described in detail, to avoid unnecessarily obscuring the new subject matter described herein. It should be clear that individual features of one or several of the specific embodiments described herein can be used in combination with features of other described embodiments or with other features. Further, like reference numbers and designations in the various drawings indicate like elements.

Referring to FIGS. 1-5, a core tissue sample cassette 100 comprises a base 102 and a lid 104 that is hinged to the base at a hinge 106 and is shown in a partway open position, extending up from the base. Base 102 includes an elongated channel 108 that is shaped and sized to accept a core tissue sample. For example, channel 108 is shaped and sized to accept a tissue sample from an 18-gauge core collector needle. In use, channel 108 is filled with a special liquid that is discussed in more detail further below. The liquid can be placed in channel 108 at a time suited to the intended use of cassette 100. For example, the liquid can be put in channel 108 when cassette 100 is manufactured and can be sealed in place, for example with adhesive or sticky tape or membrane over channel 108. Or the liquid can be put in channel 108 by a distributor when filling an order for cassettes by an end user and likewise sealed in place. Or the liquid can be put in channel 108 at a medical office that performs biopsies, and this can be done just before a biopsy procedure or more likely from time to time to prepare a supply of cassettes that are expected to be used in the foreseeable future and again sealed.

Base 102 is generally circular and can be roughly 1.75 inches in diameter. Two finger-hold indents 116, 118 at diametrically opposite locations facilitate holding cassette 100. Base 102 has a perimeter wall 120 that is generally smooth outside and is configured to accept labeling or to allow writing, for example information about a tissue sample or the patient. An upper surface of base 102 near channel 108 preferably has notation 120 that identifies the tissue sample that would be put in channel 108. This notation preferably is permanent and can be laser etched or formed in some other way. An example is the notation LMB in FIG. 1, which identifies an anatomical location of a tissue sample according to a common medical convention. As discussed further below, cassettes 100 can be provided in a set, for example 12 or more cassettes, suited for a specific medical procedure, with each cassette pre-labeled with notation 120 identifying respective anatomical locations from which samples are expected to be taken. This notation can be placed in the process of manufacturing the cassettes, for example by molding, or hot-stamping, or screen printing, or can be placed later, for example using stick-on labels when cassettes are prepared for use in a specific medical procedure. Some cassettes in the set may be left unlabeled to allow for a custom label to be placed for tissue samples taken from less common anatomical locations or targeted locations. Alternative or additional labels may be placed at the bottom or base 102. Base 102 preferably is a medium dark color, such as blue, to provide a contrasting background that facilitates visualizing a tissue sample.

Figure 3:
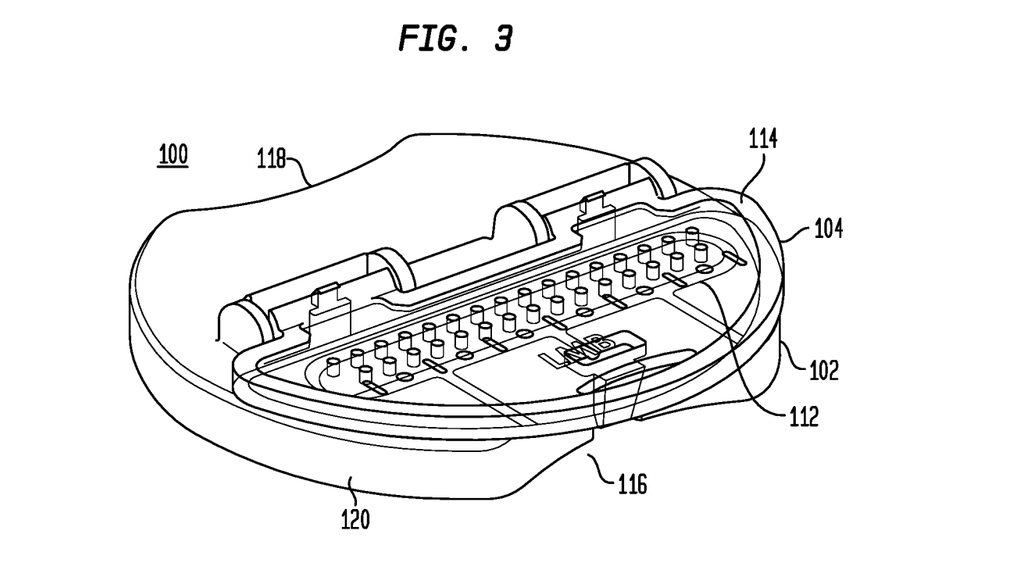
FIG. 3 is a perspective view of a cassette with a closed lid, according to some embodiments.
Figure 4:
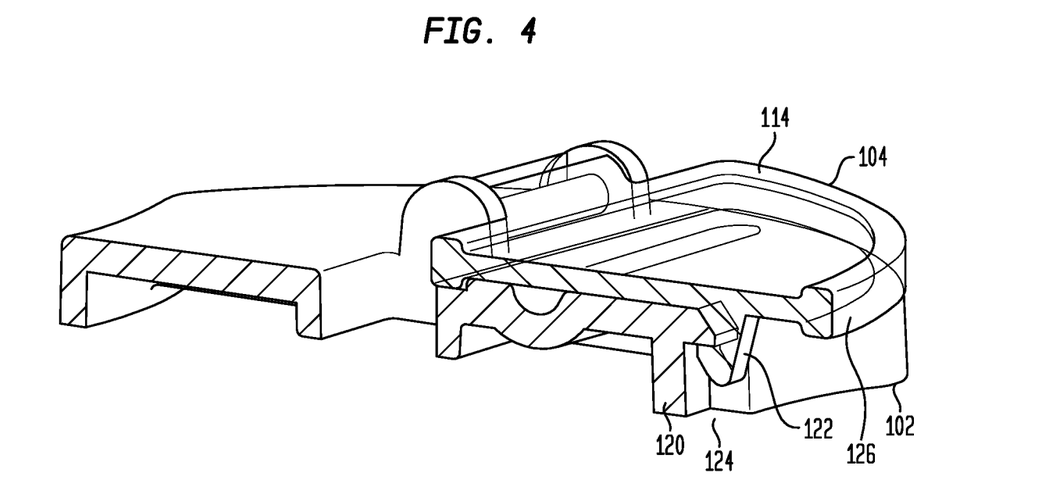
FIG. 4 is a perspective view of a portion of a cassette sectioned in a plane perpendicular to the length of a tissue sample channel, according to some embodiments.
Figure 5:
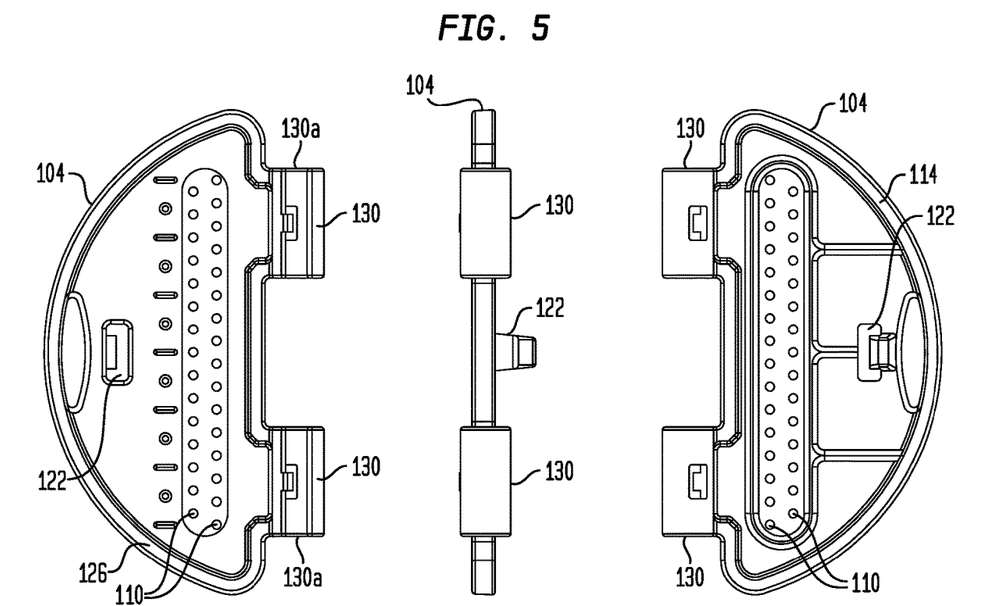
FIG. 5 shows at left a bottom view of a lid, a side view in the center, and a top view at right, according to some embodiments.

Lid 104 has an array of through holes 110 that are over channel 108 when the lid is closed (FIG. 3) and allow tissue fixative to bathe a tissue sample in channel 8 when the closed cassette 100 is immersed in tissue fixative. The bottom surface of lid 104 that surrounds holes 110 is generally flat and is configured to lie substantially flush against the top surface of base 102 surrounding channel 108. Lid 104 is transparent so that a tissue sample in channel 108 can be observed when lid 104 is closed (FIG. 3). Lid 104 has markers 112 along the array of holes 110, in two rows along the long dimension of channel 108. For example, markers 112 that are short lines are spaced 5 mm apart and markers 112 that are dots can be spaced halfway between adjacent lines so that there is a marker, either a short line or a dot, every 2.5 mm (FIG. 5). Markers 112 can be molded or otherwise formed and can assist in "grossing" a tissue sample under lid 104 while keeping the lid closed. "Grossing" refers here to a known pathology practice of visually assessing a tissue sample. Preferably, through holes 110 and markers 112 are to the side of a clear and transparent portion of lid 104 that is directly over channel 108 that allows a clear view of a tissue sample in channel 108 to facilitate grossing. A raised perimeter lip 114 around the top of lid 104 pools tissue fixative when cassette 100 is flat to keep a tissue sample in cassette 100 in fixative, for example when cassette 100 is temporarily placed on a flat surface after removal from a vessel in which it had been immersed in the fixative. Lid 104 has a snap-catch 122 protruding down and base 102 has a snap-hold 124 that releasably engage each other to hold lid 104 in a closed position for handling but to easily release and allow lid 104 to open by slight upward pressure on lid 104. When closed, lid 104 partly encircles the sidewall of base 102 with a downwardly protruding lip 126 (FIG. 4). Lid 104 preferably is transparent, but as an alternative can be made of a non-transparent material that is the same or like the material of base 102. Preferably, lid 104 and base 102 are formed (molded) separately and the lid is hinged as described below, but if as an alternative lid 104 and base 102 are formed (molded) as a single unit, the hinge arrangement described below can be replaced by a living hinge.

Base 102 preferably is molded as a single piece of a polymeric material and includes hinge pins 128. Lid 104 also is preferably molded as a single piece, of a transparent material, and has tubular snap-on extensions with a slot 130a (FIG. 5) at the bottom of the lid that snap on hinge pins 128 to thereby secure lid 104 to base 102 and allow the lid to pivot between open and closed positions. The bottom side of base 102 is generally hollow so the base is shaped as an upside-down shallow cup but may have some strengthening ribs at its underside. The sidewall of base 102 may be somewhat flared to assist in stacking cassettes 100 on top of each other.

Figure 6:
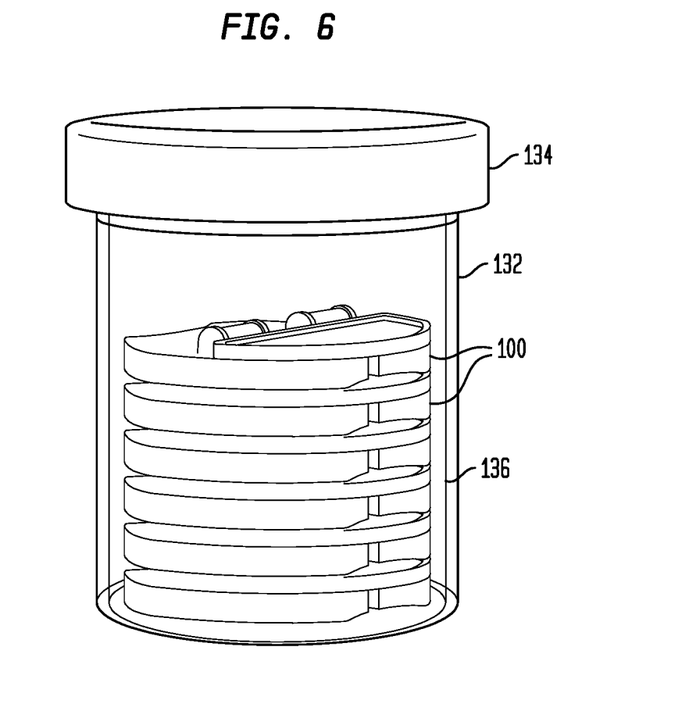
FIG. 6 illustrates a vessel enclosing a stack of tissue cassettes in formalin, according to some embodiments.

FIG. 6 illustrates a vessel 132 releasably sealed with a lid 134 that can contain tissue fixative covering a stack 136 of cassettes 100. Vessel 132 preferably is transparent and has an internal dimension that closely matches the outline of stack 136 of cassettes 100 but leaves space around the stack for flow of tissue fixative up and down the stack. Tissue fixative flow around the cassettes in the stack is further helped by providing a central opening 138 (FIG. 2) in base 102 of a cassette 100 and leaving some space around hinge 106 so that tissue fixative can flow in vessel 132 around stack 136 as well as through central openings 138 and spaces around hinge 106 and bathe the tissue samples in channels 108 though holes 110.

Figure 1:
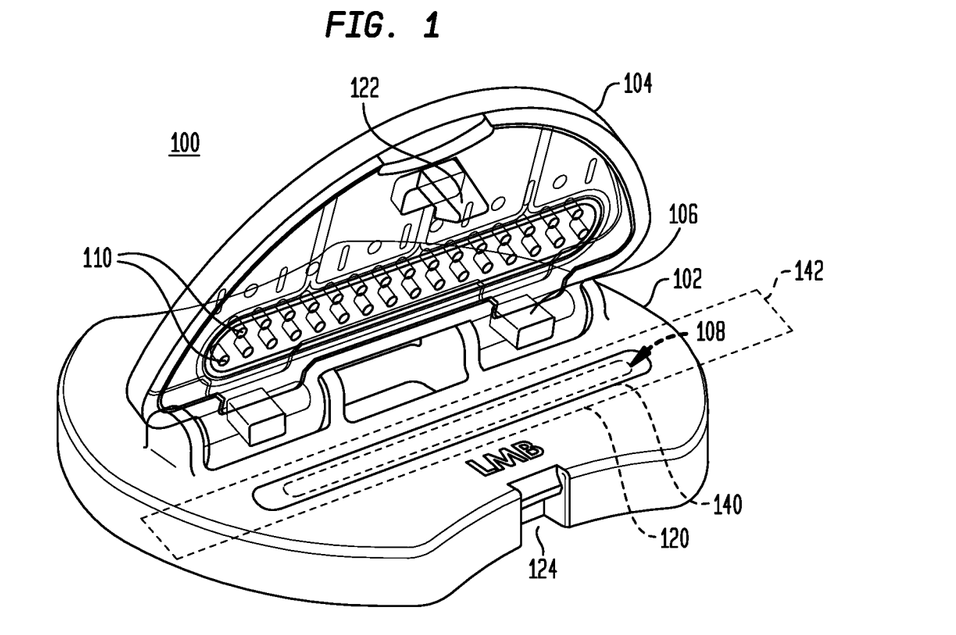
FIG. 1 is a perspective view of a core tissue sample cassette with a partway open lid, according to some embodiments.
Figure 2:
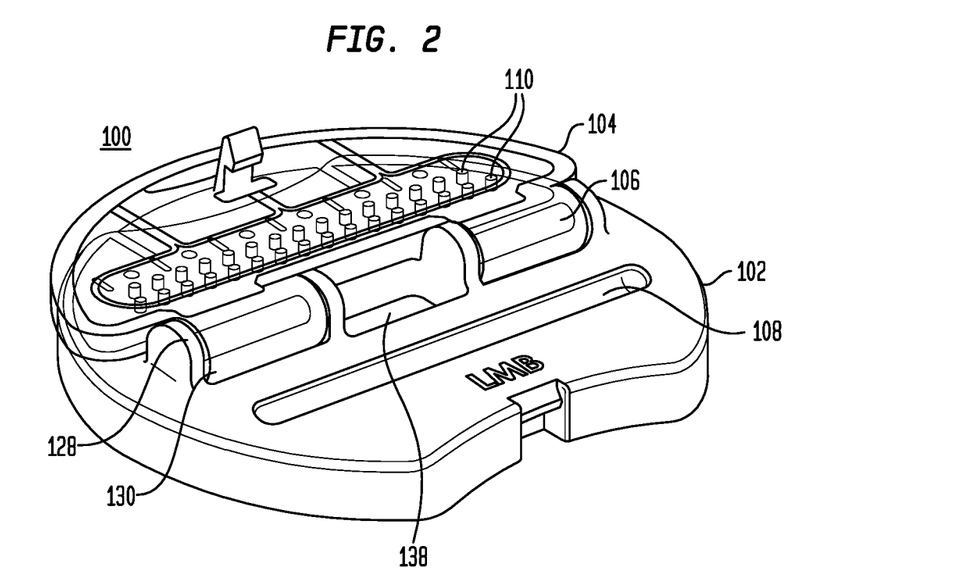
FIG. 2 is a perspective view of a core tissue sample cassette with a fully open lid, according to some embodiments.
Figure 4A:
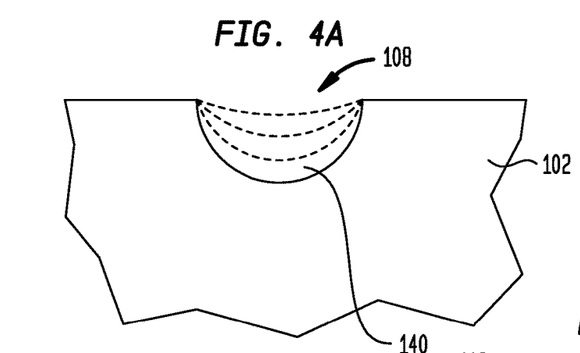
FIG. 4a is a partial sectional view of a portion of a cassette adjacent a channel and FIG. 4b is an alternative sectional view.
Figure 4B:
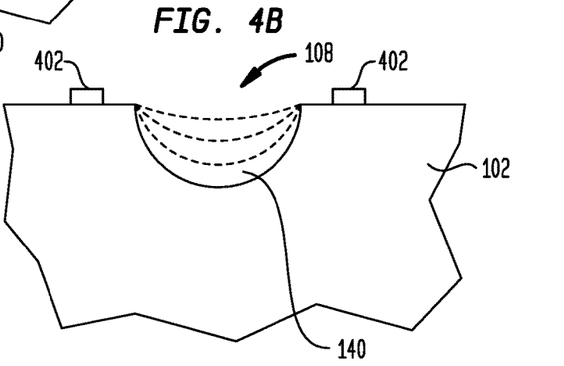

As noted, channel 108 is filled with special liquid schematically shown as liquid 140 in FIGS. 1 and 4a-4b and can be releasably sealed in place with a membrane 142 such as sticky tape over channel 108. Liquid 140 is preferably viscous, highly hydrophilic and attracts and holds a tissue sample touched to it. The mechanism of attracting and holding a tissue sample can be observed in prototype systems and is believed to involve multiple concurrent forces, not all of which are entirely understood. Applicant's current theory is that the forces of attraction and coherence between the hydrophilic surface of the liquid-lined channel and the special liquid are greater than the forces of coherence between the special liquid and the tissue sample allowing the tissue sample to be easily removed from the liquid-lined channel when needed. Likewise, the forces of attraction and cohesion between the tissue sample in the channel and the special liquid lining the channel are greater than those between the tissue sample and the inner wall of the core collector holding the sample, allowing the tissue sample to be easily transferred from the core collector to the liquid-lined channel using a simple touch-and-go process without the need for mechanical tools that can damage the sample. Applicant's current theory is that this mechanism is driven primarily by from surface tension and the forces of attraction between the hydrophilic liquid 140 and the naturally hydrous/hydrophilic properties of tissue samples comprising of cells, extracellular matrix, and interstitial liquid. The surface tension between special liquid 140 and a tissue surface that typically is hydrous and hydrophilic is believed to act as an attractant to drive contact and cohesion. As a result, these forces of attraction and cohesion drive combine to pull the tissue sample from a core collector needle into liquid 140 in channel 108 in a touch-and-go operation of touching an exposed surface of a tissue sample to liquid 140. The following references, which are incorporated herein by reference, discuss hydrogels; (1) Ahmed EM, Hydrogel: Preparagion, characterization, and applications: A review, Journal of Advanced Research, Cairo University, 2090-1232, 2013 Elsevier B. V, http://dx.doi.org/10.1016/j.jar.2013.07.006, and (2) Jakab K., Marga F., Norotte C., Murphy, Vunjak-Novakovic, Forgacs G., Tissue engineering by self-assembly and bio-printing of living cells, Biofabrication. 2010 Jun.; 2(2):022001. Doi:10.1088/1758-5085/2/2/022001. Applicant has found that a viscous liquid that currently is commercially available from Alcon Inc. of Forth Worth, TX, USA under the designation Systane Ultra Lubricant works well as special liquid 140. When special liquid 140 fills a channel 108, the top level of the liquid can be to the top edge of the channel or below the top edge so long as there is sufficient liquid in the channel to help attract and hold a tissue sample in a touch-and-go motion. Another exemplary substance suitable for the special liquid 140 is commercially available from Medline Industries, LP of Northfield, IL under the designation Medline Skintegrity Hydrogel. The special liquid has viscosity higher than that of water at room temperature (1 centipoise (cps) according to https://www.smooth-on.com/page/viscosity-scale/) but less than that of peanut butter or tomato sauce (100,000-150,000 according to the same website). Preferably, the viscosity at room temperature (20 degrees Centigrade) is in the range 3-25,000 cps, more preferably in the 3-10,000 cps range, still more preferably in the 3-3,000 cps range, still more preferably in the 3-300 cps range, and still more preferably in the 3-15 cps range. The viscosity of Systane is reported to be in the 3.09-11.64 cps (see https://www.aaopt.org/detail/knowledge-base-article/ph-osmolality-and-viscosity-artificial-tears).

FIG. 4a illustrates in dotted lines several possible levels of special liquid 140 lining channel 108, to the top or to lower levels to only partly fill channel 108. FIG. 4b is like FIG. 4a but shows an alternative in which an upwardly extending rim surrounds channel 108 such that when lid 104 is closed over a tissue sample in channel 108 it would not crush or compress the tissue sample.

In typical use of cassette 100, a physician uses a biopsy instrument to capture a tissue sample as known, withdraws the core collector from the patient and hands the instrument to an assistant. The assistant retracts the cutting sheath to expose the tissue sample that is in a notch in the core collector needle and touches an exposed surface of the tissue sample to liquid 140 in channel 108. Typically, this involves a touch-and-go motion that does not require forceful wiping the tissue sample against the cassette and simply lets the tissue sample separate from the core collector needle and rest in channel 108. Of course, at that time lid 104 is open, any membrane or tape 142 over channel 108 has been removed beforehand, and there is sufficient liquid 140 present in channel 108. Once the tissue sample is in channel 108, the assistant pivots and snaps lid 104 closed and hands the biopsy instrument back to the physician if additional samples are to be taken. As noted, this touch-and-go action preserves tissue sample integrity much better than a known method of wiping a tissue sample on a foam pad or using devices such as forceps to remove a tissue sample from a core needle collector and placing it on a foam pad or to rearrange a sample on a foam pad. In addition, applicant has found that the touch-and-go action speeds the process compared with the known method of wiping a sample on a foam pad and preparing it for sending to pathology. The assistant stacks the cassettes in a tissue fixative vessel (FIG. 6), seals the vessel and prepares it for sending to pathology. A physician may perform initial grossing before the cassettes are put in the vessel. In a pathology lab, the cassettes are processed to treat the tissue samples as needed, and that process too is speeded up compared to treating tissue samples on foam pads, as the lab personnel receive samples the integrity of which has been preserved and orientation of which is apparent from the way they are in cassettes 100. Practitioners have informed applicant that grossing samples on foam can take as much as 5 minutes per sample and typically includes having to straighten and rearrange the sample but grossing the already straight and integral sample in a cassette 100 saves 2-3 minutes per sample or as much as half-hour for a complete set of tissue samples. The sample can be processed in the usual manner in a standard tissue processor while remaining in cassette 100, and the processed sample can be removed from cassette 100 and embedded in paraffin much more efficiently than a processed sample taken from a foam pad or filter paper that may require straightening and rearranging. Experience has shown applicant that the processing and paraffin embedding step using cassettes 100 can save an additional 2-3 minutes per sample in the lab.

Figure 7:
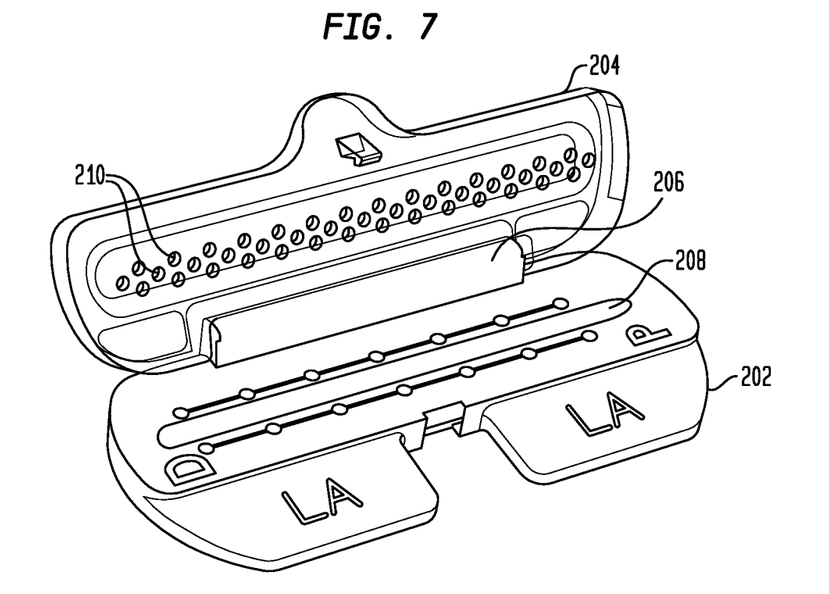
FIG. 7 illustrates an alternative example of a tissue sample cassette, according to some embodiments.

FIG. 7 illustrates an alternative cassette 200 that has a base 202 with a channel 208 that can be the same as channel 108 or can vary in depth from a shallow proximal end to a deeper distal end. Channel 208 can be filled completely or partly with liquid 140 (not shown) that can be releasably sealed in the channel with a membrane or tape (not shown) like tape 142 (FIG. 1). Lid 204 is hinged at 206 to pivot between being open as seen in FIG. 7 and closed and has an array of through holes 210 like holes 110. At its underside, an area surrounding holes 210 is flat and is flush against a flat area surrounding channel 208 when lid 204 is closed. Lid 204 and base 202 have a snap-catch arrangement like that of cassette 100 so that lid 202 is securely but releasably held to base 202 when the lid is closed.

Figure 8:
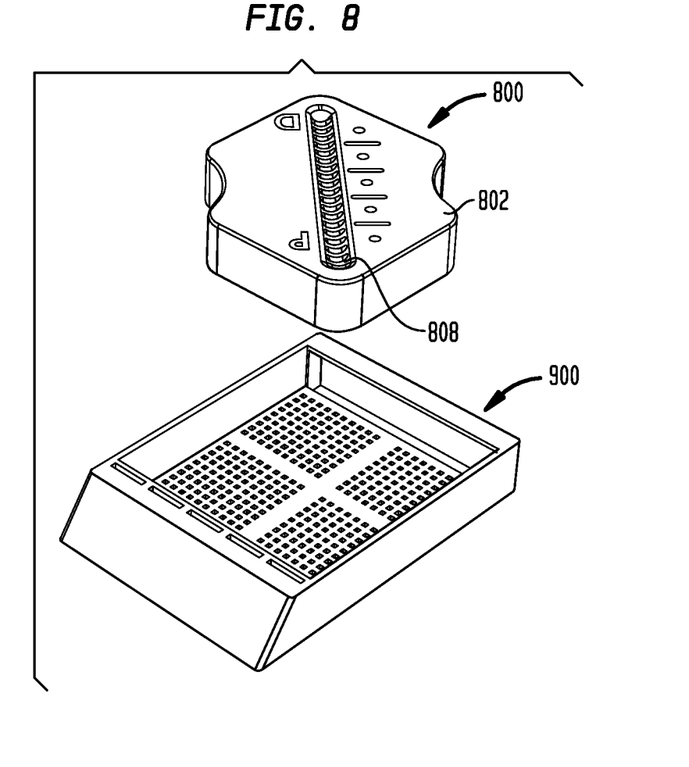
FIG. 8 is a perspective view of another tissue holder according to some embodiments that is configured to fit in a known cassette.
Figure 9:
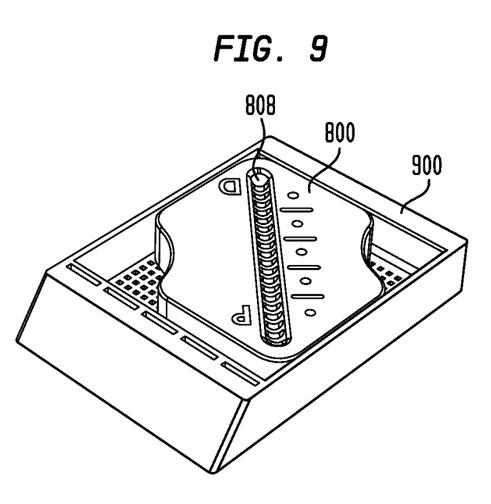
FIG. 9 is a perspective view of the tissue holder of FIG. 8 placed in a known cassette, according to some embodiments.
Figure 10:
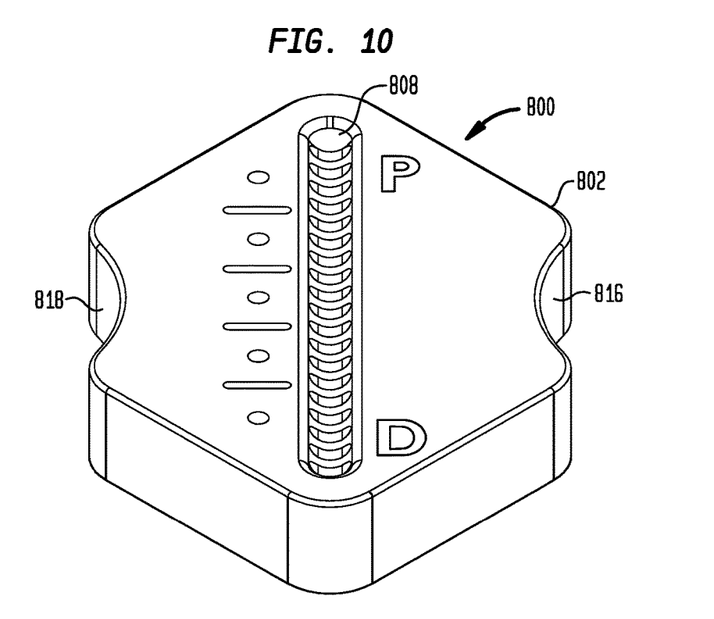
FIG. 10 is another perspective view of the tissue holder of FIGS. 8 and 9, according to some embodiments.

FIGS. 8-11b illustrate another alternative embodiment. In which a new tissue sample holder 800 is configured to fit in a known cassette 900, such as a cassette available from Leica Biosystems Inc. of Buffalo Grove, IL FIG. 8 shows in perspective tissue holder 800 and cassette 900 separate from each other and FIG. 9 shows tissue sample holder 800 fitted in cassette 900. Tissue cassette 800 comprises a base 802 with a channel 808 that is like channel 108 in FIGS. 1-5 and serves like functions. Notably, channel 808 is configured to extend diagonally when in cassette 800, thereby allowing channel 808 to accommodate tissue samples longer than the length of a side of known cassette 900. Base 802 has finger holds 816, 818 that facilitate handling tissue holder 808 and are like finger holders 116 and 118 in the embodiments of FIGS. 1-7.

Figure 11A:
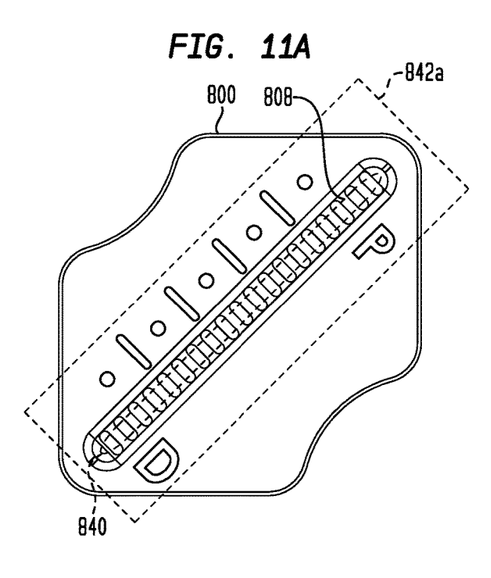
FIG. 11a is a top view and FIG. 11b is a bottom view of the tissue sample of FIGS. 8-10.
Figure 11B:
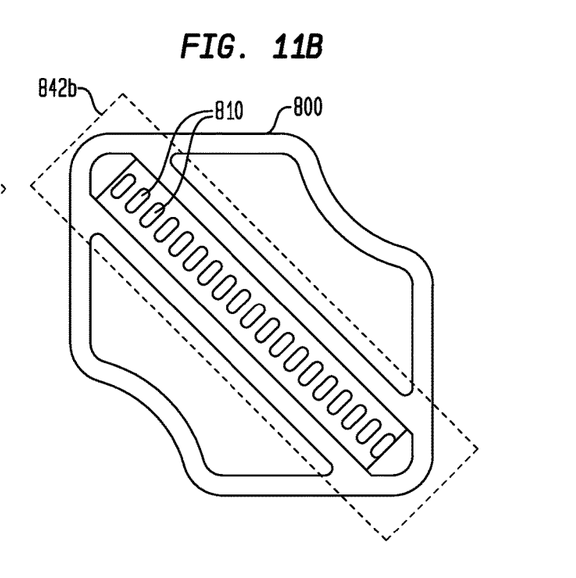

As best seen in FIGS. 11a-b, channel 808 has a row of through-holes 810 that allow for fixative flow through the bottom side of channel 808 and around a tissue sample in channel 808. Preferably, the row of through-holes 810 extends along substantially the entire length of channel 808. In typical use, a membrane 842b is taped at the bottom side of tissue holder, over the row of through-holes 810 to temporarily prevent liquid flow through holed 810. Special liquid 840 is placed in channel 88 to line the channel, as in the case channel 108. A membrane 842a can be placed over the top side of channel 808 to seal the top of the channel and keep special liquid 840 therein. Base 802 can be prepared in this manner at the manufacturing site or at a clinic where it would be used for a tissue sample. Alternatively, at the use site only a membrane 842b can be used, at the bottom side of base 802, special liquid 840 can be placed in channel 808, and to top side of channel 808 can be left uncovered, i.e., without a membrane 842a if a tissue sample is expected to be soon placed in holder 800. As another alternative, if special liquid 840 is sufficiently viscous to continue lining channel 808 when smeared therein, one or both of membranes 842a and 142b would not be used at all.

As described for the embodiment in FIGS. 1-7, in typical use an assistant removes membrane 840a (if that membrane is present) and touches an exposed side of a tissue sample to special liquid 840 lining channel 808 to thereby dislodge the sample from a tissue collector into channel 808 in the touch-and-go motion described above. The assistant places tissue holder 800, with the tissue sample in channel 808, in a cassette 900, in the configuration seen in FIG. 9. The assistant places several such combinations of a tissue holder and a cassette, with respective tissue samples therein, in a vessel of a tissue fixative that is like vessel 132 but may be differently shaped, for shipment to a pathology lab. If a membrane 842b was used over the bottom side of channel 808, it preferably is peeled off before placing the tissue holder and cassette in the tissue fixative vessel.

Although the foregoing has been described in some detail for purposes of clarity, it will be apparent that certain changes and modifications may be made without departing from the principles thereof. There can be many alternative ways of implementing both the processes and apparatuses described herein. Accordingly, the present embodiments are to be considered as illustrative and not restrictive, and the body of work described herein is not to be limited to the details given herein, which may be modified within the scope and equivalents of the appended claims or permissible revisions thereof.

The invention claimed is:

1. A system comprising:
a tissue core sample cassette having a base with an open channel configured to hold a tissue sample and lined with a special liquid configured to attract the tissue sample, wherein the channel is made of a material that is sufficiently hydrophilic for lining with said special liquid;
said cassette further comprises a removable membrane covering the channel and keeping the special liquid therein and a hinged lid configured to pivot between open and closed positions;
wherein:
said lid has an array of through holes that allow flow to and from said channel when the lid is closed and further has a bottom surface that surrounds the array of holes and, when the lid is closed, is flush with an upper surface of the base that surrounds the channel therein;
said lid is configured to releasably snap-fit to the base when closed over said membrane and to open and expose the membrane when manually pushed up from the base;
said special liquid is exposed when the lid is moved from its closed position over the membrane to its open position and the membrane is peeled off; and
said lid is transparent and has a pattern of visible markings along said array of holes that are spaced by selected distance, to facilitate grossing a tissue sample in the channel while the lid is closed; and
said lid when closed over a tissue sample in the channel is configured for flow of tissue fixative through said through holes to the sample.

2. The system of claim 1, further including a plurality of said tissue sample cassettes forming a set of cassettes and a vessel having an internal cross-section matching an outside of said cassettes but leaving space around the cassettes for tissue fixative flow and configured to hold said set of cassettes while immersed in tissue fixative.

3. The system of claim 2, in which each of one or more of said cassettes is permanently pre-labeled with an identification of an anatomical origin of a tissue sample according to a medical labeling convention.

4. The system of claim 2, in which the base of each of one or more of the cassettes in the set includes a hinge pin and the lid includes a rounded tubular element with that tightly fits over the hinge pin and has an opening configured to snap over the pin, wherein the lid and base are separately molded of respective polymeric materials and the lid is snapped over said pin to pivot about the pin between being open and closed.

5. The system of claim 2, in which the lid of each of one or more of the cassettes in the set includes an upward peripheral lip configured to pool tissue fixative.

6. The system of claim 2, in which the lid of each of one or more of the cassettes in the set includes a downward peripheral lip configured to fit over a periphery of the base.

7. The system of claim 2, in which the base of each of one or more of the cassettes in the set includes a central opening that the lid clears, which central opening facilitates flow of tissue fixative therethrough to facilitate bathing tissue samples in said cassettes when in said vessel.

8. The system of claim 2, in which the base of each of one or more of the cassettes in the set is generally round and is scalloped with one or more finger-hold indentation to facilitate handling the cassette.

9. The system of claim 2, in which said upper surface of the base surrounding the channel includes a flat surface and said base has a generally hollow underside.

10. The system of claim 2, in which the lid of each of one or more of the cassettes in the set has a flat underside surface surrounding said array of holes.

11. A tissue core sample cassette comprising:
a base with an open channel configured to hold a tissue sample and lined with a special liquid configured to attract and hold a tissue sample;
a hinged lid hinged configured to pivot between open and closed positions relative to the base;
wherein:
said lid has an array of through holes for flow to and from said channel when the lid is in its closed position and further has a bottom surface that surrounds the array of holes and when the lid is in its closed position is flush with an upper surface of the base that surrounds the channel therein;
said lid is configured to releasably snap-fit to the base when in its closed position and cover said channel to pivot to its open position and expose the channel when manually pushed up from the base;
said lid is transparent and has a pattern of visible markings along said array of through holes that are spaced by selected distance, to facilitate grossing of a tissue sample in the channel while the lid is closed; and
said lid when closed over a tissue sample in the channel is configured for flow of tissue fixative through said holes to the sample.

12. The cassette of claim 11, further including said special liquid in the channel and a removable membrane covering the channel and keeping the special liquid therein until peeled off to expose the channel and the special liquid.

13. The cassette of claim 11, in which said special liquid has the property of attracting a tissue sample touched thereto and keeping a tissue sample in the channel, is soluble in tissue fixative, and is free of substances adversely affecting sample characteristics.

14. The cassette of claim 11, in which said base includes a central opening configured for flow of tissue fixative therethrough.

15. The cassette of claim 11, in which said base is molded as a single piece and includes a hinge pin and said lid is separately molded as a single piece and includes a tubular catch with an opening configured to snap-fit over said hinge pin for pivoting thereabout.

16. The cassette of claim 11, in which said base is made of a polymeric material colored to contrast with a tissue sample in said channel.

17. The cassette of claim 11, in which said base is permanently pre-labeled with an identification of an anatomical origin of a tissue sample according to a medical labeling convention.

18. The cassette of claim 11, in which said base includes one or more finger-holds configured to facilitate handling the cassette at least when depositing a tissue sample in said channel.

19. A method of preparing tissue samples for sending to pathology comprising:
touching an exposed portion of a tissue samples in a core collector to a special liquid that lines a hydrophilic channel in a cassette base and has the property of attracting the tissue sample to dislodge the sample from the core collector and hold the sample in the channel;
snapping and releasably locking a transparent lid over the channel and the sample therein, wherein the lid has an array of through holes for flow to and from the channel when the lid is closed;
placing plural cassettes with samples therein and the lids closed in a vessel of tissue fixative having an interior shape conforming to and closely fitting the exterior shape of the cassettes but providing sufficient space around the cassettes for flow of tissue fixative up and down the vessel that bathes the samples through said through holes in the lids; and
further providing central holes in the cassette bases for flow of tissue fixative in the vessel through said central holes in the bases of the cassettes in the vessel.

20. The method of claim 19, including molding the cassette bases as single pieces of a polymeric material in a color contrasting the tissue samples and the lids as single pieces of a hard transparent plastic.

21. A holder for a core tissue sample comprising:
a base having an elongated channel with a hydrophilic surface that is open on top but closed at its ends and is configured to accept a core tissue sample;
a special hydrophilic liquid lining the channel and configured to attract a tissue sample touched to the special liquid and keep the tissue sample in the channel; and
wherein said special liquid is configured to be soluble in tissue fixative over a selected time interval and is free of substances adversely affecting sample characteristics and is further configured to easily release the sample from the channel while retaining the sample integrity.

22. The holder of claim 21, further including a transparent lid that is hinged to the base to pivot between closed and open positions and has an array of through holes for flow to and from said channel when the lid is closed.

23. The holder of claim 21, in which said channel has a depth that decreases from a proximal end to a distal end of the channel.

24. The holder of claim 21, in which said special liquid in said channel comprises a liquid that has hydrophilic and viscous characteristics matching those of a liquid currently commercially available from Alcon Inc. under the designation Systane Ultra Lubricant.

25. The holder of claim 21, in which the special liquid in the channel has a viscosity in the range of 3 to 12 centipoise.

26. The holder of claim 21, in which the special liquid in the channel has a viscosity in the range of 3 to 80,000 centipoise.

27. The holder of claim 21, in which said special liquid in said channel comprises a liquid that has hydrophilic and viscous characteristics matching those of a liquid currently commercially available from Medline Industries, LP under the designation Medline Skintegrity Hydrogel.

28. A method of dislodging a tissue sample from a notch in a core collector needle that exposes a surface of the sample into a hydrophilic channel in a tissue holder, comprising;
lining the hydrophilic channel with a special liquid that is hydrophilic;
touching an exposed surface of the tissue sample in a core collector needle to said special liquid lining the channel;
wherein the forces attracting said special liquid to the channel are greater than those attracting said tissue sample to the special liquid and the forces attracting the tissue sample to said liquid lining the channel are greater than those attracting the tissue sample to the notch in the core collector; and subsequently releasing the tissue sample from the channel without requiring physical tools to pull the sample from the channel.

29. The method of claim 28, further including covering the channel to keep therein said special liquid before dislodging a tissue sample in the channel and removing the covering to expose the special liquid lining the channel and dislodge the tissue sample from the core collector needle into the channel.

30. A system comprising:

a tissue core sample cassette having a base with an open channel configured to hold a tissue sample and lined with a special liquid configured to attract the tissue sample, wherein the channel is made of a material that is sufficiently hydrophilic for lining with said special liquid;

said cassette further comprises a removable membrane covering the channel and keeping the special liquid therein and a lid configured to move between open and closed positions;

wherein:

said lid has an array of through holes that allow flow to and from said channel when the lid is closed and further has a bottom surface that surrounds the array of holes and, when the lid is closed, is flush with an upper surface of the base that surrounds the channel therein;

said lid is configured to releasably snap-fit to the base when closed over said membrane and to open and expose the membrane when manually pushed up from the base;

said special liquid is exposed when the lid is moved from its closed position over the membrane to its open position and the membrane is peeled off; and said lid is transparent and has a pattern of visible markings along said array of holes that are spaced by selected distance, to facilitate grossing a tissue sample in the channel while the lid is closed; and said lid when closed over a tissue sample in the channel is configured for flow of tissue fixative through said through holes to the sample.

\* \* \* \* \*